United States Patent [19]

Niinaka et al.

[11] Patent Number: 5,780,418

[45] Date of Patent: Jul. 14, 1998

[54] BATHING PREPARATION

[75] Inventors: Kouichi Niinaka; Katsuhiko Takeuchi; Tetsuro Kamiya; Hidenori Yorozu, all of Tochigi, Japan

[73] Assignee: Kao Corporation, Tokyo, Japan

[21] Appl. No.: 728,499

[22] Filed: Oct. 9, 1996

[30] Foreign Application Priority Data

Oct. 11, 1995 [JP] Japan .................. 7-262721

[51] Int. Cl.⁶ .................. C11D 17/04
[52] U.S. Cl. .................. 510/439; 510/130; 510/135; 510/475; 206/484; 206/484.2; 206/524.2; 206/524.9; 206/524.7
[58] Field of Search .................. 510/439, 130, 510/135, 296, 475; 206/484, 484.2, 524.2, 524.9, 524.7

[56] References Cited

U.S. PATENT DOCUMENTS

| | | | |
|---|---|---|---|
| 3,316,190 | 4/1967 | Suzumura et al. | 260/17.4 |
| 3,630,920 | 12/1971 | Freifeld et al. | 510/439 |
| 3,798,179 | 3/1974 | Hellyer | 510/135 |
| 3,892,905 | 7/1975 | Albert | 428/220 |
| 4,747,976 | 5/1988 | Yang et al. | 510/439 |
| 4,765,916 | 8/1988 | Ogar, Jr. et al. | 252/8.9 |
| 4,806,261 | 2/1989 | Ciallella et al. | 510/296 |
| 4,844,828 | 7/1989 | Aoki | 510/439 |
| 5,041,252 | 8/1991 | Fujii et al. | 264/176.1 |
| 5,141,666 | 8/1992 | Yorozu et al. | 510/130 |
| 5,198,198 | 3/1993 | Gladfelter et al. | 510/439 |
| 5,280,835 | 1/1994 | Edwards et al. | 206/484 |
| 5,384,364 | 1/1995 | Besse et al. | 510/439 |

FOREIGN PATENT DOCUMENTS

| | | |
|---|---|---|
| 455586 | 11/1991 | European Pat. Off. . |
| 51-106183 | 9/1976 | Japan . |
| 62-072610 | 4/1987 | Japan . |
| 63-099006 | 4/1988 | Japan . |
| 08118559 | 5/1996 | Japan . |
| 09104617 | 4/1997 | Japan . |

*Primary Examiner*—Paul Lieberman
*Assistant Examiner*—Lorna M. Douyon
*Attorney, Agent, or Firm*—Oblon, Spivak, McClelland, Maier & Neustadt, P.C.

[57] ABSTRACT

A bathing preparation is disclosed, comprising bathing agent components packed in a bag which is made of; a nonwoven or woven fabric consisting of a water soluble polymer fiber or a laminate sheet comprising a nonwoven or woven fabric consisting of a water soluble polymer fiber on the outside and a water soluble film on the inside.

8 Claims, No Drawings

BATHING PREPARATION

FIELD OF THE INVENTION

This invention relates to a bathing preparation packed in a bag which is excellent in storage stability and solubility in bathwater.

BACKGROUND OF THE INVENTION

There are bathing preparations of various types including powders, tablets, etc. It is convenient to package bathing agent components in a single dosage in a water soluble polymer material and put it as such into a bathtub, since it is unnecessary in this case to measure the bathing preparation each time.

Examples of such bathing preparations include those composed of bathing agent components packaged in a water soluble polymer film "Hicelon" marketed by The Nippon Synthetic Chemical Industry, Co., Ltd. or films made of partially saponified polyvinyl acetate, polyvinyl alcohol partial butyrate, vinyl pyrrolidone/vinyl acetate copolymer, etc. (JP-A-50-126008; the term "JP-A" as used herein means an "unexamined published Japanese Patent application").

Further, there have been proposed a product composed of liquid bathing agent components (e.g., bath oil, etc.) packaged in a polyvinyl alcohol film of about 30 to 50 μm in thickness and 40 to 60 g/m² in weight (JP-A-58-188813); a bathing preparation-packing bag composed of a hydrogel biopolymer in the form of a sheet coated with a fusible water soluble synthetic resin (JP-A-60-158060); a bathing preparation composed of bathing agent components packed in a bag made of a water soluble sheet of pullulan or pullulan and polyvinyl alcohol and/or polyvinyl pyrrolidone (JP-A-62-72610); a bathing preparation-packing bag composed of a foatmable bathing composition packed in a water soluble bag comprising polyvinyl alcohol, carboxymethyl cellulose, 4,4,6-tri-glucopolysaccharide, etc. as the main components (JP-A-63-99006); a packaged bathing preparation wherein a bathing preparation is packed in a film obtained from a solution of a mixture comprising gelatin and starch as the major components (JP-A-2-202812); and a bathing preparation obtained by coating moisture-free plants with natural water-soluble polymers (e. g., starch, mannan, algae, viscous matters originating in plants, proteins, gelatin, etc.), synthetic water-soluble polymers (e.g., polyvinyl alcohol, sodium polyacrylate, polyethylene oxide, etc.) or semisyntihetic water-soluble polymers (e.g., methyl cellulose, carboxymiethyl cellulose, soluble starch, carboxymethyl starch, etc.) (JP-A-4-103521).

However, the bathing preparation for such a conventional water soluble packing bag is thinned so as to elevate the solubility in bathing water, which brings about some problems, for example, a poor mechanical strength, difficulties in the production process, a poor storage stability (i.e., becoming sticky or being deteriorated in texture and solubility) when stored for a long time in a highly humid place such as a bathroom, lavatory, etc.

SUMMARY OF THE INVENTION

Accordingly, an object of the present invention is to provide a bathing preparation packed in a bag which is excellent in storage stability and can be quickly dissolved.

Under these circumstances, the present inventors have conducted extensive studies. As a result, they have successfully found out that a bathing preparation with the use of a bag made of a nonwoven or woven fabric consisting of a water soluble polymer fiber is excellent in storage stability and solubility, thus completing the present invention.

Accordingly, the present invention provides a bathing preparation comprising bathing agent components packed in a bag which is made of a nonwoven or woven fabric consisting of a water soluble polymer fiber.

DETAILED DESCRIPTION OF THE INVENTION

Preferable examples of the water soluble polymer fiber used in the present invention include fibers of polyvinyl alcohol, polyvinyl pyrrolidone, pullulan, carboxyrtethyl cellulose, hydroxypropyl cellulose, etc. Among these, a polyvinyl alcohol fiber is still preferred. The polyvinyl alcohol may be one which has been modified with maleic acid, itaconic acid, etc. It is particularly preferable to use a polyvinyl alcohol fiber made of polyvinyl alcohol having a degree of polymerization of 100 to 3,000.

It is preferable that the water soluble polymer fiber is soluble in water at 0° to 50° C., still preferably 0° to 10° C., or miscible therewith. The expression "soluble or miscible" as used herein means that 0.5 g of the fiber is dissolved in 1 liter of water at 50° C. or miscible therewith within 10 minutes and gives no residue after passing through a sieve No. 8.6 (pharmacopoeia; 2,000 μm). The diameter of the water soluble polymer fiber preferably ranges from 5 to 200 μm, still preferably from 5 to 50 μm.

It is preferable that the nonwoven or woven fabric of the water soluble polymer fiber is one which is highly soluble or dispersible in water at a low temperature and scarcely shrinks (i.e., having a low shrinkage percentage) even under a high humidity.

Examples of such the nonwoven fabric include those made of water soluble polyvinyl alcohol fibers disclosed in JP-A-5-321105, JP-A-7-42019, JP-A-3-86530, JP-A-3-279410, JP-A-3-199408 and JP-A-2-112406.

It is also possible to arbitrarily control the dissolution time of the bag in bathing water by appropriately varying the characteristics of the polymer material, or the conditions for processing the nonwoven or woven fabric. The weight of the nonwoven fabric, etc. per unit area may be appropriately determined depending on fiber. In the case of a polyvinyl alcohol fiber, the weight preferably ranges from 2 to 200 g/m², still preferably from 25 to 100 g/m². The thickness of the nonwoven fabric preferably ranges from 10 to 3,000 μm, still preferably from 25 to 400 μm. On the other hand, the thickness of the woven fabric preferably ranges from 20 to 2,000 μm, still preferably from 50 to 500 μm.

It is also possible that the nonwoven or woven fabric is heat-pressed either entirely or partly (for example, dotted) so as to regulate the air-permeability or embossed so as to improve the texture or enhance the strength.

In the present invention, it is preferable that the bathing preparation comprises of bathing agent components packed in a bag which is made of a laminate film comprising a nonwoven or woven fabric consisting of a water soluble polymer fiber on the outside and a water soluble film on the inside.

Examples of the water soluble film to be used inside include those made of water soluble polymers such as polyvinyl alcohol, modified polyvinyl alcohol derivative prepared by copolymerizing itaconic acid, maleic acid, etc., polyvinyl pyrrolidone, carboxymethyl cellulose, gelatin, starch, soluble starch, pullulan, mannan, algae, viscous matters originating in plants, sodium polyacrylate, methyl cellulose, carboxymethyl cellulose, carboxymethyl starch, etc. It is preferable that such the film has a thickness of from 5 to 200 μm.

The water soluble film may be laminated onto the nonwoven or woven fabric by placing the film on one face of the nonwoven or woven fabric followed by adhesion due to heat-sealing, etc. Alternatively, the water soluble polymer may be applied onto one face of the nonwoven or woven fabric to thereby form a film.

The bathing-packing bag to be used in the bathing preparation of the present invention may be formed by folding the above-mentioned nonwoven or woven fabric or laminate sheet in two followed by adhesion on three sides, or laying two pieces of the sheet one on top of another followed by adhesion on four sides. The adhesion may be conveniently performed by heat-sealing. It is also possible to fuse the sheet with the use of a water soluble polymer such as polyvinyl alcohol or polyethylene glycol or to stitch it with the use of a water soluble thread made of, for example, polyvinyl alcohol or modified polyvinyl alcohol. Alternatively, the bathing preparation may be wrapped in a nonwoven fabric sheet in such a manner as to form a sack and then sealed by heat-sealing, fusing the opening with the use of a water soluble polymer or stitching or tieing with a water soluble thread, as described above. Namely, the bathing preparation may be processed into various forms.

The bathing preparation-packing bag thus obtained may be printed with various patterns by using water soluble inks, if required.

The bathing agent components to be packed in the bathing preparation-packing bag are not particularly restricted but selected from among those commonly employed in bathing preparations. Examples thereof include inorganic salts such as sodium chloride, sodium hydrogencarbonate, sodium carbonate, boric acid, borax, sodium sulfate, sodium sulfide, potassium nitrate, sodium nitrate, calcium nitrate, ammonium sulfate, potassium chloride, ammonium chloride, sodium phosphate and magnesium sulfate; organic acids such as citric acid, fumaric acid, tartaric acid, malic acid and benzoic acid; polyhydric alcohols such as propylene glycol, glycerol, 1,3-butylene glycol, polyethylene glycol and saccharose; vitamins, enzymes, plant components, surfactants, perfumes, etc. Among these, a bathing preparation comprising carbonates such as sodium hydrogencarbonate and sodium carbonate is preferable and one comprising these carbonates as the major components is still preferable.

The bathing agent components to be packed may be in an arbitrary form such as powders, granules, tablets, capsules, etc. When the bathing preparation is in the form of a powder, it is preferable that at least 80% by weight of particles thereof fall within a particle size range of from 20 to 300 μm.

In the bathing preparation of the present invention, the bathing agent components are packed in a bag, thus, it is not necessary to measure the product each time. Further, the bathing preparation sustains its inherent texture without becoming sticky and shows a high solubility even after storing under a high humidity.

EXAMPLES

To further illustrate the present invention in greater detail, and not by way of limitation, the following Examples will be given.

Example 1

In accordance with the formulation given in Table 1, the raw materials were mixed, heated to 60° C. and then granulated with an extrusion granulator to thereby give granular bathing agent components. Next, a bathing preparation-packing bag (9 cm×9 cm) made of a nonwoven fabric consisting of a polyvinyl alcohol (degree of polymerization: 1,700) fiber as specified below was produced by heat-sealing and then the above-mentioned granular bathing agent components were packed therein to thereby give a bathing preparation of a single dosage of 30 g.

[Data of nonwoven fabric]

Diameter of fiber: 15 μm

Dissolution temperature of fiber: 5° C.

Thickness of nonwoven fabric: 280 μm

Metsuke (weight per unit area $g/m^2$) of nonwoven fabric: 50 $g/m^2$

Examples 2 and 3

In accordance with the formulation given in Table 1, the raw materials were mixed and sieved to thereby give bathing agent components wherein at least 80% by weight of the particles thereof fell within a particle size range of from 20 to 200 μm. Next, a bathing preparation-packing bag (8 cm×8 cm) made of a nonwoven fabric consisting of a polyvinyl alcohol (degree of polymerization: 1,700) fiber as specified below was produced by heat-sealing and then the above-mentioned granular bathing agent components were packed therein to thereby give a bathing preparation of a single dosage of 30 g.

Data of nonwoven fabric:

Diameter of fiber: 15 μm

Dissolution temperature of fiber: 5° C.

Thickness of nonwoven fabric: 280 μm Metsuke ($g/m^2$) of nonwoven fabric: 50 $g/m^2$

Example 4

In accordance with the formulation given in Table 1, the raw materials were mixed and then tableted under applying pressure to thereby give bathing agent components in the form of a tablet. Next, a bathing preparation-packing bag (9 cm×9 cm) made of a nonwoven fabric consisting of a polyvinyl alcohol (degree of polymerization: 1,700) fiber as specified below was produced by heat-sealing and then the above-mentioned mentioned bathing agent components in the form of a tablet were packed therein to thereby give a bathing preparation of a single dosage of 30 g.

[Data of nonwoven fabric]

Diameter of fiber: 15 μm

Dissolution temperature of fiber: 5° C.

Thickness of nonwoven fabric: 280 μm

Metsuke ($g/m^2$) of nonwoven fabric: 50 $g/m^2$

Examples 5 to 8

The procedures of Examples 1 to 4 were repeated, respectively, except for replacing each bag with one made of a nonwoven fabric consisting of a maleic acid-modified polyvinyl alcohol (degree of polymerization: 1700) fiber as specified below to thereby give a bathing preparation of a single dosage of 30 g.

[Data of nonwoven fabric]

Diameter of fiber: 15 4μm

Dissolution temperature of fiber: 1° C.

Thickness of nonwoven fabric: 280 μm

Metsuke ($g/m^2$) of nonwoven fabric: 50 $g/m^2$

Examples 9 to 12

The procedures of Examples 1 to 4 were repeated, respectively, except for replacing each bag with one made of a laminate sheet comprising a nonwoven fabric (outside) consisting of a polyvinyl alcohol (degree of polymerization: 1700) fiber as specified below and a polyvinyl alcohol (degree of polymerization: 1500) film (inside) having a thickness of 35 μm to thereby give a bathing preparation of a single dosage of 30 g.

[Data of nonwoven fabric]

Diameter of fiber: 15 μm

Dissolution temperature of fiber: 5° C.

Thickness of nonwoven fabric: 170 μm Metsuke (g/m$^2$) of nonwoven fabric: 25 g/m$^2$

Example 13

The procedures of Example 5 was repeated, respectively, except for replacing the bag with one made of a laminate sheet comprising a nonwoven fabric (outside) consisting of a maleic acid-modified polyvinyl alcohol (degree of polymerization: 1400) fiber as specified below and an itaconic acid-modified polyvinyl alcohol (degree of polymerization: 1500) film (inside) having a thickness of 35 μm to thereby give a bathing preparation of a single dosage of 30 g.

[Data of nonwoven fabric]

Diameter of fiber: 15 μm

Dissolution temperature of fiber: 1° C.

Thickness of nonwoven fabric: 170 μm

Metsuke (g/m$^2$) of nonwoven fabric: 25 g/m$^2$

Examples 14 to 16

The procedures of Examples 6 to 8 were repeated, respectively, except for replacing each bag with one made of a laminate sheet comprising a nonwoven fabric (outside) consisting of a maleic acid-modified polyvinyl alcohol (degree of polymerization: 1400) fiber as specified below and a polyvinyl alcohol (degree of polymerization: 1500) film (inside) having a thickness of 35 μm to thereby give a bathing preparation of a single dosage of 30 g.

[Data of nonwoven fabric]

Diameter of fiber: 15 μm

Dissolution temperature of fiber: 1° C.

Thickness of nonwoven fabric: 170 μm

Metsuke (g/m$^2$) of nonwoven fabric: 25 g/m$^2$

Comparative Examples 1 to 4

The procedures of Examples 1 to 4 were repeated, respectively, expect for replacing each bag with one made of a polyvinyl alcohol (degree of polymerization: 1500) film having a thickness of 35 μm to thereby give a bathing preparation of a single dosage of 30 g.

TABLE 1

| Composition (wt. %) | Ex. 1 | Ex. 2 | Ex. 3 | Ex. 4 |
| --- | --- | --- | --- | --- |
| Sodium hydrogen carbonate | 28.5 | 90.5 | 5.2 | 35.5 |
| Sodium carbonate | the balance | ← | ← | ← |
| Sodium sulfate | | 5.2 | 90.5 | |
| Glucose | 10.0 | | | 42.8 |
| Polyethylene glycol | 19.0 | | | 3.6 |
| Alum | 3.0 | | | |
| Dextrin | | | | 0.3 |
| Cationized cellulose | 0.1 | | | |
| Jojoba oil | | 0.1 | 0.1 | |
| Perfume | 0.4 | 1.0 | 1.0 | 0.4 |
| Colorant | trace | ← | ← | ← |
| Total | 100.0 | 100.0 | 100.0 | 100.0 |

Test Example

The bathing preparations obtained in the above Examples 1, 4, and 9 to 12 and Comparative Examples 1 to 4 were each evaluated in the storage stability (texture of bag, stickiness) and solubility in bathwater (dissolution time in 150 liter of tap water at 40° C. under stirring once in 5 seconds) immediately after production and after storing under a high humidity (40° C., 75% RH, 24 hours), based on the following evaluation criteria.

The results are shown in Table 2 below.

Evaluation criteria:

| Texture | Stickiness | Dissolution time |
| --- | --- | --- |
| E: good | E: not sticky | time required for the dissolution of bathing agent component packed in bag |
| G: somewhat good | G: little sticky | |
| P: somewhat poor | P: somewhat sticky | |
| B: poor | B: sticky | |

TABLE 2

| | Storage stability of bag | | Dissolution in water (time) | |
| --- | --- | --- | --- | --- |
| | Immediately after production | After storing under high humidity | Immediately after production | After storing under high humidity |
| Ex. 1 | texture E stickiness E | texture E stickiness E | 40 sec | 45 sec |
| Ex. 4 | texture E stickiness E | texture E stickiness E | 3 min | 4 min |
| Ex. 9 | texture E stickiness E | texture E stickiness E | 42 sec | 46 sec |
| Ex. 10 | texture E stickiness E | texture E stickiness E | 17 sec | 20 sec |
| Ex. 11 | texture E stickiness E | texture E stickiness E | 18 sec | 20 sec |
| Ex. 12 | texture E stickiness E | texture E stickiness E | 3 min | 4 min |
| C.Ex. 1 | texture G stickiness G | texture P stickiness P | 40 sec | 80 sec |
| C.Ex. 2 | texture G stickiness G | texture P stickiness P | 15 sec | 60 sec |
| C.Ex. 3 | texture G stickiness G | texture P stickiness P | 15 sec | 50 sec |
| C.Ex. 4 | texture G stickiness G | texture P stickiness P | 3 min | 6 min |

As is apparent from the results of Table 3, it has been found out that a bathing preparation comprising bathing agent components packed in a water soluble packing bag having a high storage stability under a high humidity, which cannot be achieved by the conventional product, can be obtained by using a bag made of a nonwoven or woven fabric consisting of a water soluble polyvinyl alcohol fiber or a laminate sheet comprising a nonwoven or woven fabric consisting of a water soluble polyvinyl alcohol fiber and a water soluble film. From the viewpoint of solubility, it has been also proved that the product of the present invention has an effect of preventing the prolongation of the dissolution time after storing under a high humidity which cannot be achieved by the conventional products.

While the invention has been described in detailed and with reference to specific embodiments thereof, it will be apparent to one skilled in the art that various changes and modifications can be made therein without departing from the spirit and scope thereof.

What is claimed is:

1. A packaged bathing preparation comprising bathing agent components packed in a bag which is made of a laminate sheet comprising a nonwoven or woven fabric consisting of a water soluble, polyvinyl alcohol polymer fiber on the outside and a water soluble film on the inside.

2. The packaged bathing preparation as claimed in claim 1 wherein said fabric is a nonwoven fabric.

3. The packaged bathing preparation as claimed in claim 1, wherein said water soluble polyvinyl alcohol polymer fiber is one soluble in water at 0° to 50° C. or miscible therewith.

4. The packaged bathing preparation as claimed in claim 1 wherein said polyvinyl alcohol polymer fiber is soluble in water at a temperature in the range of 0° to 10° C. or miscible therewith.

5. A packaged bathing preparation as set forth in claim 1 wherein said polyvinyl alcohol polymer fiber has a dissolution temperature in the range of 1° C. to 5° C.

6. The packaged bathing preparation as claimed in claim 1, wherein said bathing agent components are in the form of granules.

7. The packaged bathing preparation as claimed in claim 1, wherein said bathing agent components are in the form of a powder.

8. The packaged bathing preparation as claimed in claim 1, wherein said bathing agent components are in the form of a tablet.

* * * * *